United States Patent

Shaw

[11] 3,969,416
[45] July 13, 1976

[54] PREPARATION OF KETALS

[76] Inventor: Peter Sylvester Shaw, Cross Farm, Orton Rigg, Great Orton, Cumberland, England

[22] Filed: May 9, 1974

[21] Appl. No.: 469,011

Related U.S. Application Data

[63] Continuation of Ser. No. 249,837, May 3, 1972, abandoned.

[30] Foreign Application Priority Data

May 4, 1971 United Kingdom............. 12869/71

[52] U.S. Cl............................ 260/615 A; 260/340.5
[51] Int. Cl.²................... C07C 41/10; C07C 41/06
[58] Field of Search..................... 260/615 A, 614 A

[56] References Cited
UNITED STATES PATENTS

| | | | |
|---|---|---|---|
| 2,000,252 | 5/1935 | Repe et al......................... | 260/615 A |
| 2,480,940 | 9/1949 | Leum............................... | 260/614 A |
| 3,024,284 | 3/1962 | Howard et al. .................. | 260/614 R |
| 3,121,124 | 2/1964 | Verdol............................. | 260/614 A |
| 3,170,000 | 2/1965 | Verdol............................. | 260/614 A |

FOREIGN PATENTS OR APPLICATIONS 957,000 4/1964 United Kingdom.............. 260/614 A Primary Examiner—Howard T. Mars
Attorney, Agent, or Firm—Wenderoth, Lind & Ponack

[57] ABSTRACT

An unsaturated compound of formula

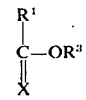

in which $R^1$ and $R^3$ represent alkyl groups of 1 to 4 carbon atoms and XH is $R^2$ which represents a primary or secondary alkyl group of 1 to 4 carbon atoms, is reacted with an alkanol of formula $R^4OH$, in which $R^4$ represents a normal alkyl group of 1 to 4 carbon atoms, in the presence of, as catalyst, a strong cation exchange resin in the acid form, to produce a ketal of formula

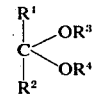

which may be used in the synthesis of pesticides.

7 Claims, No Drawings

PREPARATION OF KETALS

This is a continuation, of application Ser. No. 249,837, filed May 3, 1972, now abandoned.

The present invention relates to the production of certain ketals.

The invention provides a process for the preparation of a ketal of the formula

wherein
$R^1$ represents an alkyl group of 1 to 4 carbon atoms (eg methyl, ethyl or n-butyl);
$R^2$ represents a primary or secondary alkyl group of 1 to 4 carbon atoms (eg methyl, ethyl or n-butyl);
$R^3$ represents an alkyl group of 1 to 4 carbon atoms (eg methyl, ethyl, n-propyl, isopropyl, n-butyl or secondary butyl); and
$R^4$ represents a normal alkyl group of 1 to 4 carbon atoms (eg methyl or ethyl);
which process comprises reacting an unsaturated compound of the formula

where
$R^1$ and $R^3$ are as defined above and XH equals $R^2$ (i.e. X represents the corresponding alkylidene group), with an alkanol of the formula $R^4OH$, in the presence of, as catalyst, a strong ion exchange resin in the acid form.

This process is of particular importance when operated in conjunction with a process for preparing a 4-hydroxy-benzodioxole of the formula

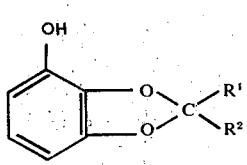

wherein $R^1$ and $R^2$ are as defined above, which process comprises reacting pyrogallol with a ketal of formula I. These 4-hydroxy-benzodioxoles can be used to prepare pesticides such as 2,2-dimethyl-1,3-benzodioxol-4-yl N-methylcarbamate, eg by reaction with methyl isocyanate. In the process for preparing a 4-hydroxy-benzodioxole, the unsaturated compound of formula II may be produced as by-product:

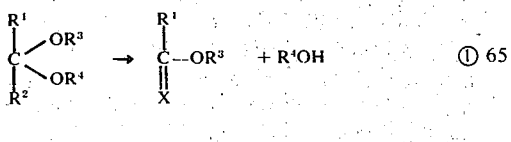 ① where $R^1$, $R^2$, $R^3$, $R^4$ and X are as defined above. The present invention enables the unsaturated compound to be recombined with alkanol of 1 to 4 carbon atoms, and in a particularly convenient way, and then recycled. After recombination, the ion exchange resin can readily be separated, eg by filtration or decanting or by employing a column of the resin down which reactants are passed. Removal of the resin is desirable since its presence mars the reactions of pyrogallol with a ketal of formula I producing the 4-hydroxy-benzodioxole. Before recycling, removal of any excess alkanol $R^4OH$ is also desirable, eg by fractionating or, preferably, by extraction with a neutral salt solution such as saturated calcium chloride solution or preferably saturated sodium sulphate solution.

Since water may have an adverse effect on the product of the present process, it may in some instances be desirable to dry the resin, eg at 110°C for an hour. In view of the small resin: liquid ratio normally used, however, even large percentages of water in the resin generally have but little effect.

Sulphonic acid ion exchange resins in the acid form are suitable resins. The present ion exchange resin must be sufficiently strongly acid to catalyse the reaction, eg as strong as the sulphonic acid ion exchange resins. Suitable strong cation exchange resins in the acid form are the sulphonic acid cross linked polystyrene ion exchange resins in the acid form. Specific examples of suitable resins are the acid form of Amberlite IR 120 or Zeo-Karb 325.

The present reaction is suitably conducted in an inert solvent, eg inert solvent in which the unsaturated compound of formula II is present after reaction ①. Such a solvent may for example have a boiling point in the range 90° to 150°C, eg 100° to 150°C. Toluene, xylene or tetrachloroethylene are suitable, especially toluene and most preferably xylene. The solvent may be a mixture of compounds.

The reaction is suitably conducted in the range 10°–60°C. Preferably the essential materials are brought into contact with one another at ambient temperature. As the reaction is exothermic, cooling may be desirable if the amount of the unsaturated compound is large.

Preferably, the mol ratio of alkanol to unsaturated compound is at least 1:1.

Usually, the amount of catalyst is at least 0.1%, preferably at least 0.6% by weight of the unsaturated compound. For reasons of economy, the amount of catalyst (calculated in the dried state) is usually no more than 12% by weight of the unsaturated compound.

Preferably, $R^4$ represents a methyl or ethyl group, especially a methyl group.

Usually $R^3$ and $R^4$ are the same and preferably they represent methyl groups. $R^1$ and $R^2$ are also usually the same as each other, and preferably both represent methyl groups.

Thus, in a particular embodiment of the present process 2-methoxy-propene is reacted with methanol to form 2,2-dimethoxypropane:

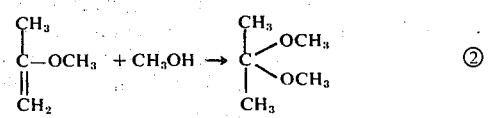 ②

The invention is illustrated by the following Examples, in which percentages are by weight unless otherwise indicated.

EXAMPLES 1 and 2

100 G portions of liquid mixtures, initially at 20°C, whose compositions are given in the Table below, the remainder being toluene, were agitated under reflux condensers with 2% weight/volume of the dried acid form of Amberlite IR 120 sulphonic acid ion exchange resin. The temperature rises recorded and the compositions of the mixtures after reaction are also given in the Table. Analyses were by gas liquid chromatography.

| Temperature rise °C. | Example 1 25 | | | | Example 2 55 | | | |
|---|---|---|---|---|---|---|---|---|
| | Before reaction | | After reaction | | Before reaction | | After reaction | |
| Substance | g. | g.mols | g. | g.mols | g. | g.mols | g. | g.mols |
| Methanol | 16 | 0.50 | 11 | 0.345 | 18 | 0.56 | 3 | 0.094 |
| 2-methoxypropene | 17 | 0.237 | 0 | 0 | 34 | 0.473 | 0 | 0 |
| 2,2-dimethoxypropane | 12 | 0.115 | 35 | 0.34 | 26 | 0.250 | 74 | 0.71 |

EXAMPLES 3, 4 and 5

To stirred 50 ml. portions of a mixture of toluene, 2,2-dimethoxypropane, 2-methoxypropene (16% w/w) and excess methanol at 21°C. were added 0.1, 0.5 and 2% w/v of the dried acid form of Amberlite IR 120 sulphonic acid ion exchange resin. The times taken for complete reaction of the 2-methoxypropene were 15, 5 and 3 minutes respectively.

EXAMPLE 6

126 gms. (1 g. mol) of pyrogallol was dissolved in 208 gms. (2 g.mols) of hot 2,2-dimethoxypropane, and toluene (875 mls.) was added. Then, while distilling for 10 hours, maintaining the temperature of the reaction mixture at 110°C, 1,925 mls. of distillate was collected and a further 9.2g. mols of 2,2-dimethoxypropane and 525 mls. toluene were added to the reaction mixture. Negligible pyrogallol remained and the residue weighed 650g. and contained by GLC (gas liquid chromatographic) analysis, 142 gms, equivalent to 86% yield from pyrogallol, of 2,2-dimethyl-4-hydroxy-1,3-benzodioxole.

The distillate from the ketal exchange reaction contained some 2-methoxypropene as well as methanol, 2,2-dimethoxypropane and toluene. The 2-methoxypropene was recombined with equivalent methanol by the addition of, as catalyst, 2% weight/volume dried acid form Amberlite 120 sulphonic acid exchange resin with external water cooling. The distillate was then found to contain, by GLC analysis, 9.32g. mols of 2,2-dimethoxypropane, so that the net usage was 1.88g. mols., and the yield of 2,2-dimethyl-4-hydroxy-1,3-benzodioxole from net 2,2-dimethoxypropane was 50%. The distillate, after decanting from the resin and removing methanol by aqueous alkali or preferably aqueous sodium sulphate extraction, could then be dried, and recycled to the ketal exchange stage.

EXAMPLE 7

1.g. mol (126 g.) of pure grade pyrogallol (containing less than 0.3% water) was dissolved by heating with agitation in 1.125 g. mols (117 g, 138 mls) of 2,2-dimethoxypropane and 525 mls of toluene. The resulting mixture was distilled at the rate of 140 mls per hour, adding toluene at the same rate, until the reaction mixture reached 115°C. This took about 1½ hours. Then, 1.875 g. mols (195 g, 231 mls) of 2,2-dimethoxypropane were pumped in below the liquid level, over a period of 4¼– 4½hours, allowing the temperature to rise to 120°C, while distilling at 110 mls per hour. The weight of the reaction mixture was not allowed to fall below 450g., toluene being added to maintain this minimum weight. After all the 2,2-dimethoxypropane had been added, distillation was continued until the vapor temperature was at least 102°C (indicating that negligible 2,2-dimethoxypropane remained in the reaction mixture). Analysis revealed that not more than 2% of the initial pyrogallol remained unreacted. The residue weighed 500 g.

The distillate, after standing for less than a day, was agitated, under a reflux condenser, with 0.2% weight/volume of dried (at 105°C) acid form Amberlite 120 sulphonic acid ion exchange resin. The mixture was then cooled to not more than 25°C and decanted off from the ion exchange resin. Methanol and part of any acetone were removed by one extraction with an equal volume of 16% by weight NaOH in water.

The aqueous extract was boiled to a vapor temperature of 100°C to remove solvents and the residue was recycled after adding water to adjust to 16% by weight NaOH.

The organic layer from the extraction stage was dried by extracting with ¼ the volume of 48% by weight NaOH in water, and then fractionated and the fractions containing pure 2,2-dimethoxypropane and/or toluene recycled to the ketal exchange stage.

EXAMPLE 8

Example 7 was repeated but using 0.4% weight/volume of acid form Amberlite 120 sulphonic acid ion exchange resin containing 50% by weight of water, in place of the 0.2% weight/volume dried ion exchange resin. The yield of 2,2-dimethoxypropane in the catalysed reaction was unaffected.

EXAMPLE 9

(a) 1 g. mol (126 g.) of pure grade pyrogallol was mixed with 1.125 g mols (117 g., 138 mls.) of 2,2-dimethoxypropane and 525 mls of xylene (mixed isomers). The mixture was heated to boiling over 20 minutes, then distilled at 130 mls/hr. (i) for 1 hour, adding xylene at the same rate, and then (ii) for 4 hours, meanwhile adding 95 mls of xylene and pumping in below the liquid level 1.64 g mols of 2,2-dimethoxypropane.

The residue (500 g.) was distilled down to 413 g. and found to contain, by analysis, negligible pyrogallol and 152 g., equivalent to a 92% yield, of 2,2-dimethyl-4-hydroxy-1,3-benzodioxole.

(b) The residue was cooled primary 45°C., a trace (½ ml.) of triethylamine added, then in two lots, with cooling between 1.1 g. mols of methyl isocyanate was added thereto. After 4 hours agitation at 20°–25°C, isopropylamine (4mls) was added to destroy the unreacted methyl isocyanate. After agitating for 1 hour further, the precipitate was filtered off, washed with 100 mls of xylene and dried giving 192 g., representing an 86% yield, of 2,2-dimethyl-1,3-benzodioxol-4-yl N-methylcarbamate.

(c) The distillate from stage a) was agitated for ½ hour under a reflux condenser with 0.2% weight/volume Amberlite 120 sulphonic acid ion exchange resin, cooled to 25°C. and the resin removed. After 2 extractions with an equal volume of saturated aqueous sodium sulphate solution at 18°C, then drying over sodium sulphate, the xylene solution contained, by analysis, 124g. of 2,2-dimethoxypropane and was suitable for recycling to stage a).

I claim:

1. A process for the preparation of a ketal of the formula

 (I)

wherein
$R^1$ is alkyl of 1 to 4 carbon atoms,
$R^2$ is a primaru or secondary alkyl group of 1 to 4 carbon atoms,
$R^3$ is methyl and
$R^4$ is methyl,
which comprises reacting an unsaturated compound of the formula

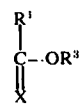 (II)

wherein $R^1$ and $R^3$ are as defined above and X is a primary or secondary alkylidene group of 1 to 4 carbon atoms, with methanol in the presence of an inert solvent and a sulphonic acid ion exchange resin in the acid form as catalyst, at a temperature of 10°–60°C.

2. A process according to claim 1 wherein the exchange resin in the acid form is a sulphonic acid cross linked polystyrene ion exchange resin in the acid form.

3. A process according to claim 1 wherein the reaction is conducted in an inert solvent for the unsaturated compound, the solvent having a boiling point in the range 90° to 150°C.

4. A process according to claim 3 wherein the solvent is selected from the group consisting of toluene, xylene and tetrachloroethylene.

5. A process according to claim 1 wherein $R^1$ and $R^2$ are the same.

6. A process according to claim 1 wherein $R^1$ and $R^2$ each represent methyl.

7. A process for the preparation of 2,2-dimethoxypropane, which comprises reacting at 10°– 60°C 2-methoxypropene with methanol in the presence of an inert solvent selected from the group consisting of toluene, xylene and tetrachloroethylene, and in the presence as catalyst of at least 0.1% by weight of the 2-methoxypropene of a sulphonic acid ion exchange resin in the acid form.

* * * * *